(12) United States Patent
Rangisetty et al.

(10) Patent No.: US 7,179,939 B2
(45) Date of Patent: Feb. 20, 2007

(54) SODIUM FERRIC GLUCONATE COMPLEXES AND METHOD OF MANUFACTURE THEREOF

(75) Inventors: Jagadeesh Babu Rangisetty, Lawrenceville, NJ (US); Christopher Benny Newton, Plainsboro, NJ (US)

(73) Assignee: Navinta LLC, Ewing, NJ (US)

( * ) Notice: Subject to any disclaimer, the term of this patent is extended or adjusted under 35 U.S.C. 154(b) by 162 days.

(21) Appl. No.: 10/889,123

(22) Filed: Jul. 12, 2004

(65) Prior Publication Data

US 2005/0209322 A1  Sep. 22, 2005

Related U.S. Application Data

(60) Provisional application No. 60/554,004, filed on Mar. 16, 2004.

(51) Int. Cl.
*C07C 59/10* (2006.01)

(52) U.S. Cl. .................................................. 562/587

(58) Field of Classification Search ............... 568/512, 568/580, 579, 700, 840, 902, 913, 918, 919
See application file for complete search history.

(56) References Cited

U.S. PATENT DOCUMENTS

| | | | |
|---|---|---|---|
| 2,820,740 A | 1/1958 | London et al. | |
| 2,885,393 A | 5/1959 | Herb et al. | |
| 6,537,820 B2 | 3/2003 | Beck et al. | 436/84 |
| 6,693,211 B2 | 2/2004 | Kumari et al. | 556/146 |
| 2002/0076821 A1 | 6/2002 | Beck et al. | 436/74 |
| 2003/0153086 A1 | 8/2003 | Beck et al. | 436/74 |
| 2003/0216566 A1* | 11/2003 | Kumari et al. | 536/123.13 |

FOREIGN PATENT DOCUMENTS

| | | |
|---|---|---|
| GB | 1133863 | 11/1908 |
| WO | WO 03/098564 | 11/1903 |
| WO | WO 2005/000210 A2 | 1/2005 |

OTHER PUBLICATIONS

Perry's Chemical Engineers' Handbook (7th Edition) Edited by: Perry, R.H.; Green, D.W.© 1997 McGraw-Hill, pp. 22:73-74.*
Kirk-Othmer Encyclopedia of Chemical Technology Copyright© 2003 by John Wiley & Sons, Inc. Article Online Posting Date: Mar. 14, 2003, pp. 321-397.*

(Continued)

*Primary Examiner*—Thurman K. Page
*Assistant Examiner*—Karl Puttlitz
(74) *Attorney, Agent, or Firm*—Drinker Biddle & Reath LLP; Daniel A. Monaco

(57) ABSTRACT

A process is provided for preparing a sodium ferric gluconate complex, substantially free of excipients, for providing a sodium ferric gluconate complex co-precipitated with sucrose, and for providing sodium ferric gluconate complexes in aqueous solution.

63 Claims, 6 Drawing Sheets

OTHER PUBLICATIONS

Spiro et al., The Hydrolytic Polymerization of Iron (III), *J. Am. Chem. Soc.*, 88:12, 1966, 2721.

Mehltretter et al., Sequestration by Sugar Acids; *Industrial And engineering Chemistry*, vol. 45 (12), 2782-2784, 1953.

Pecsok et al., The Gluconate complexes II: The Ferric-gluconate System, *Journal of the American Chemical Society* (1955), 77, 1489-94.

Panda et al., Gluconate Complexes of Aluminum(III) and Iron(III), *Journal of the Institution of Chemists* (India) (1977), 49(6), 297-301.

Tanabe et al., Iron complexes I: Analytical Studies on Ferric-gluconic Acid Chelates, *Takeda Pharm. Inds., Ltd., Oksaka, Yakugaku Zasshi* (1958), 78, 951-7, Japanese with English abstract.

\* cited by examiner

SODIUM FERRIC GLUCONATE COMPLEXES AND METHOD OF MANUFACTURE THEREOF

CROSS-REFERENCE TO RELATED APPLICATION

This application claims the benefit of now abandoned U.S. Provisional Application Ser. No. 60/554,004, filed Mar. 16, 2004, the entire disclosure of which is herein incorporated by reference.

FIELD OF THE INVENTION

The present invention relates to a process for making sodium ferric gluconate complexes.

BACKGROUND OF THE INVENTION

A. Intravenous Iron Therapy

Iron therapy is necessary to replenish total body iron stores in patients with iron deficiency anemia. Therapeutically-active iron-containing compositions comprise iron in a form capable of increasing the amount of hemoglobin in the blood. Intravenous (IV) is particularly employed for patients who cannot tolerate oral iron therapy, are unable to adequately absorb dietary iron, or who suffer hematopoietic failure.

B. Potential Side Effects of IV Iron Therapy

One iron formulation, iron dextran, has been associated with significant adverse effects. Such effects are reported in approximately 26% of patients receiving iron dextran. See, Gupta et al., *Kidney Int.*, 1999 May; 55(5):1891–8. The underlying cause of the immediate severe reactions is unclear. However, known anaphylactic reactions to dextran have implicated dextran as the cause of the severe reactions to IV iron dextran. IV iron products free of dextran are thought to decrease or avoid these severe reactions.

One product that is dextran-free is sodium ferric gluconate complex in sucrose (FERRLECIT®). Reactions associated with administration of sodium ferric gluconate are mild to moderate and occur at a lower rate compared to reactions associated with iron dextran. The most common reactions associated with sodium ferric gluconate are transient hypotension, flushing, rash, and gastrointestinal symptoms. See, Nissenson et al., *Am. J. Kidney Dis.* 1999 March; 33(3):471–82. One study comparing iron dextran with sodium ferric gluconate has shown an occurrence of 3.3 allergic episodes per million doses for sodium ferric gluconate and 8.7 allergic episodes per million doses for iron dextran. Id.

C. Purity of Sodium Ferric Gluconate Complexes

Since the 1975 merger of the United States Pharmacopoeia (USP) with the National Formulary (NF) to produce the USP-NF compendial guidelines for drugs, standard identities and analytical protocols have been developed for over 3,800 pharmaceuticals. Still, 35% of marketed pharmaceuticals, including sodium ferric gluconate complex in sucrose, are not included in the USP-NF.

Sodium ferric gluconate complex in sucrose generally contains contaminants including excipients, free gluconate and by-products of the synthesis of the complex which are readily detected by techniques such as gel permeation chromatography (GPC).

A chromatographic method for separating and purifying an iron saccharidic complex product is disclosed in U.S. Patent Application Publications 2002/0076821 and 2003/0153086. A sodium ferric gluconate complex, substantially free of excipients having a molecular weight of less than about 5,000 Daltons, is also disclosed.

Small variations in molecular structure and composition can determine the difference between an active iron complex having no adverse effects, and another iron complex that may induce adverse reactions. See, "Raising the Bar for Quality Drugs", pp. 26–31, *Chemical and Engineering News*, American Chemical Society, Mar. 19, 2001, the entire disclosure of which is incorporated herein by reference. There is a reported correlation between toxicity of iron saccharate complexes and higher molecular weight and the variability of size of the complex. See, Fishbane et al., *Semin Dial.* 2000 Nov–Dec; 13(6):381–4.

A composition of sodium ferric gluconate complex comprising a narrower molecular weight distribution may yield a safer and more efficacious therapy. There exists a need for a sodium ferric gluconate complex preparative method that results in a product with narrower molecular weight distribution as compared to existing compositions.

SUMMARY OF THE INVENTION

According to one embodiment of the invention there is provided a process of preparing sodium ferric gluconate complex, substantially free of excipients, comprising the steps of:

(a) reacting ferric hydroxide, a sodium base and sodium gluconate, in an aqueous reaction mixture, at a selected molar ratio of sodium gluconate to ferric hydroxide, for a selected time interval, at a selected temperature and at a pH in the range from about 7.5 to about 13; and (b) isolating sodium ferric gluconate complex from the aqueous reaction mixture by;

(i) forming a mixture by adding to the aqueous reaction mixture at least one water-miscible organic solvent in an amount sufficient to precipitate sodium ferric gluconate complex from the mixture; and (ii) collecting the precipitated sodium ferric gluconate complex, from the mixture formed in step (i).

According to one embodiment, the step (ii) of collecting the precipitated sodium ferric gluconate complex comprises filtration of the mixture formed in step (i).

According to another embodiment the step (ii) of collecting the precipitated sodium ferric gluconate complex comprises centrifugation of the mixture formed in step (i).

The selected molar ratio of sodium gluconate to ferric hydroxide in the aqueous reaction mixture is preferably from about 0.2:1 to about 5:1, more preferably from about 1:1 to about 5:1, most preferably from about 1:1 to about 3:1.

The pH of the aqueous reaction mixture is preferably in the range from about 7.5 to about 12, more preferably from about 7.5 to about 10, most preferably from about 7.5 to about 9. The selected temperature of the aqueous reaction mixture is a temperature in the range from about 75° C. to about 120° C., preferably in the range from about 95° C. to about 115° C.

The selected time interval is preferably in the range from about 2 minutes to about 36 hours, more preferably from about 2 minutes to about 300 minutes.

The reaction mixture may be concentrated prior to the step of isolating the sodium ferric gluconate complex to reduce the volume of the reaction mixture to a volume that is preferably in the range from about 20% to about 80% of the original volume thereof, more preferably in the range from about 20% to about 70% of the original volume thereof.

According to one embodiment of the invention, the weight average molecular weight of the isolated sodium ferric gluconate complex is in the range from about 20,000 to about 700,000 Daltons, preferably from about 20,000 to about 400,000 Daltons, more preferably, in the range from about 20,000 to about 120,000 Daltons, most preferably in the range from about 30,000 to about 90,000 Daltons. According to certain sub-embodiments of the invention, the weight average molecular weight of the prepared sodium ferric gluconate complex is about 30,000, about 35,000, about 40,000, about 50,000, about 55,000, about 60,000, about 65,000, about 70,000, about 75,000, about 80,000, about 85,000, about 90,000, about 95,000, about 100,000, about 350,000, about 500,000 or about 700,000 Daltons.

According to some sub-embodiments of the invention, the reaction mixture from about 0.2% wt/wt to about 8% wt/wt based on the weight of the reaction mixture.

According to one preferred embodiment of the invention, the ferric hydroxide used to form the sodium ferric gluconate complex according to the invention is prepared by reacting at least one ferric salt, preferably, ferric chloride, ferric nitrate, or a mixture thereof, with at least one base in a reaction mixture comprising an aqueous medium.

The collected sodium ferric gluconate complex is optionally purified, such as by:

(a) dissolving the isolated sodium ferric gluconate complex in an aqueous solvent to form a solution;

(b) forming a mixture by adding to the solution of sodium ferric gluconate complex at least one water-miscible organic solvent in an amount sufficient to precipitate sodium ferric gluconate complex from the solution; and (c) separating the purified sodium ferric gluconate complex from the mixture formed in step (b).

The purified sodium ferric gluconate complex is optionally dried.

According to one embodiment of purification of the collected sodium ferric gluconate complex, the step of separating the purified precipitated sodium ferric gluconate complex comprises filtration of the mixture formed in step (b).

According to another embodiment of purification of the collected sodium ferric gluconate complex, the step of separating the purified precipitated sodium ferric gluconate complex comprises centrifugation of the mixture formed in step (b).

According to another embodiment of the invention there is provided a process of preparing an aqueous solution of sucrose and sodium ferric gluconate complex, comprising the steps of:

(a) reacting ferric hydroxide, a sodium base and sodium gluconate, in an aqueous reaction mixture, at a selected molar ratio of sodium gluconate to ferric hydroxide, for a selected time interval, at a selected temperature and at a pH in the range from about 7.5 to about 13; and (b) isolating sodium ferric gluconate complex from the aqueous reaction mixture by;

(i) forming a mixture by adding to the aqueous reaction mixture at least one water-miscible organic solvent in an amount sufficient to precipitate sodium ferric gluconate complex from the mixture; and (ii) collecting the precipitated sodium ferric gluconate complex, from the mixture formed in step (i);

(c) dissolving the isolated sodium ferric gluconate complex in an aqueous solvent to form a solution;

(d) forming a mixture by adding to the solution formed in step (c) at least one water-miscible organic solvent in an amount sufficient to precipitate sodium ferric gluconate complex from the solution;

(e) collecting purified sodium ferric gluconate complex from the mixture formed in step (d); and (f) dissolving the purified sodium ferric gluconate complex, prepared according to step (e), in a solution of sucrose in water, preferably in a 20% solution of sucrose in water.

According to another embodiment of the invention there is provided a process of preparing a co-precipitate comprising sodium ferric gluconate complex and sucrose, the process comprising the steps of:

(a) reacting ferric hydroxide, a sodium base and sodium gluconate, in an aqueous reaction mixture, at a selected molar ratio of sodium gluconate to ferric hydroxide, for a selected time interval, at a selected temperature and at a pH in the range from about 7.5 to about 13; and (b) isolating sodium ferric gluconate complex from the aqueous reaction mixture by;

(i) forming a mixture by adding to the aqueous reaction mixture at least one water-miscible organic solvent in an amount sufficient to precipitate sodium ferric gluconate complex from the mixture; and (ii) collecting the precipitated sodium ferric gluconate complex, from the mixture formed in step (i);

(c) dissolving the isolated sodium ferric gluconate complex in an aqueous solvent to form a solution;

(d) forming a mixture by adding to the solution formed in step (c) at least one water-miscible organic solvent in an amount sufficient to precipitate sodium ferric gluconate complex from the solution;

(e) collecting the purified sodium ferric gluconate complex from the mixture formed in step (d);

(f) dissolving purified sodium ferric gluconate complex product prepared according to step (e) in an aqueous sucrose solution;

(g) forming a mixture by adding to the solution of sodium ferric gluconate complex formed in step (f) at least one water-miscible organic solvent in an amount sufficient to co-precipitate sodium ferric gluconate complex and sucrose;

(h) collecting the co-precipitate formed in step (g); and optionally (i) drying the co-precipitate.

The ratio of purified ferric gluconate complex to aqueous sucrose solution in step (f) is preferably in the range of from about 1:0.5 to about 1:10 by weight, more preferably in the range of from about 1:0.5 to about 1:5 by weight. The concentration of the sucrose solution employed to produce the co-precipitate is preferably in the range from about 10% to about 50% weight/volume of sucrose in water.

According to another embodiment of the invention there is provided a process of preparing an aqueous solution of sucrose and sodium ferric gluconate complex, comprising (a) reacting ferric hydroxide, a sodium base and sodium gluconate, in an aqueous reaction mixture, at a selected molar ratio of sodium gluconate to ferric hydroxide, for a selected time interval, at a selected temperature and at a pH in the range from about 7.5 to about 13; and (b) isolating sodium ferric gluconate complex from the aqueous reaction mixture by;

(i) forming a mixture by adding to the aqueous reaction mixture at least one water-miscible organic solvent in an amount sufficient to precipitate sodium ferric gluconate complex from the mixture; and (ii) collecting the precipitated sodium ferric gluconate complex, from the mixture formed in step (i);

(c) dissolving the isolated sodium ferric gluconate complex in an aqueous solvent to form a solution;

(d) forming a mixture by adding to the solution formed in step (c) at least one water-miscible organic solvent in an amount sufficient to precipitate sodium ferric gluconate complex from the solution;

(e) collecting the purified sodium ferric gluconate complex from the mixture formed in step (d);

(f) dissolving the purified sodium ferric gluconate complex formed in step (e) in an aqueous sucrose solution;

(g) forming a mixture by adding to the sodium ferric gluconate complex solution formed in step (f) at least one water-miscible organic solvent in an amount sufficient to co-precipitate sodium ferric gluconate complex and sucrose;

(h) collecting the co-precipitate formed in step (g); and (i) dissolving the collected co-precipitate in water.

According to another embodiment of the invention there is provided a process of preparing an aqueous solution of sucrose and sodium ferric gluconate complex, comprising the steps of:

(a) combining ferric hydroxide and sodium gluconate, in an aqueous reaction mixture, at a selected molar ratio of sodium gluconate to ferric hydroxide, at a selected temperature and at a pH in the range from about 7.5 to about 13, preferably from about 7.5 to about 12, more preferably from about 7.5 to about 10, most preferably from about 7.5 to about 9;

(b) maintaining the reaction mixture at the selected temperature for a time interval from about 2 minutes to about 36 hours, preferably from about 2 to about 300 minutes; and (c) adding to the reaction mixture a selected quantity of sucrose.

The selected temperature of the aqueous reaction mixture is preferably a temperature in the range from about 75° C. to about 120° C., more preferably in the range from about 95° C. to about 115° C., and the selected molar ratio of sodium gluconate to ferric hydroxide is preferably in the range from about 1:4 to about 5:1, more preferably in the range from about 1:1 to about 5:1, most preferably, in the range from about 1:1 to about 3:1.

The quantity of sucrose added in step (c) is preferably from about 1 to about 50 times the amount of ferric hydroxide used in step (a), on a mol/mol basis, more preferably from about 1 to about 20 times the amount of ferric hydroxide used in step (a), on a mol/mol basis.

The sodium ferric gluconate complexes prepared according to the process of the invention comprises from about 1 to about 55% ferric iron, preferably from about 1 to about 50% ferric iron (wt/wt). According to some particularly preferred embodiments, the sodium ferric gluconate complexes prepared according to the process of the invention comprise from about 1 to about 15% ferric iron, most preferably about 5% ferric iron (wt/wt). According to other particularly preferred embodiments, the sodium ferric gluconate complexes prepared according to the process of the invention comprise from about 30 to about 50% ferric iron, most preferably about 47% ferric iron (wt/wt).

According to another embodiment of the invention, there is provided a pharmaceutical composition in a solid dosage form, comprising a pharmaceutically acceptable carrier and a sodium ferric gluconate complex having a molecular weight in the range from about 20,000 to about 700,000 Daltons.

Preferably, the pharmaceutical composition of the invention comprises a sodium ferric gluconate complex prepared by the process according to the present invention.

DEFINITIONS

The expression, "substantially free of excipients," used to describe the product sodium ferric gluconate complex formed by the method of the invention means that the product contains about 5% (wt/wt) of excipients or less, and correspondingly contains about 95% (wt/wt) or more sodium ferric gluconate complex.

The term "excipients" as used herein refers to components of the product of a process of the invention that are other than sodium ferric gluconate complex. Examples include, free gluconate, water and solvents.

The expression "weight average molecular weight" unless otherwise indicated, is one expression of the molecular weight of a substance which comprises a distribution of molecular weights rather than a single molecular weight. The "weight average molecular weight" is calculated as a summation of the squares of the weights of a fraction of the molecular weight distribution, divided by the total weight of the molecules. The weight average molecular weight may be determined by gel permeation chromatography (GPC) using refractive index, light scattering, small angle neutron scattering (SANS), or by sedimentation velocity.

The expression "alkali metal," as employed herein refers to metals or ions of metals found in Group I of the periodic table. Preferred alkali metals are lithium, sodium and potassium.

The term "base" as employed herein refers to a chemical species that donates electrons or hydroxide ions (Arrhenius definition) or that accepts protons (Brönsted definition). Bases include strong bases, i.e., bases that are completely dissociated in aqueous solution and weak bases, i.e., bases that are only partially dissociated in aqueous solution. Examples of strong bases include sodium hydroxide and potassium hydroxide. Examples of weak bases include ammonia and alkyl amines.

The expression "sodium base" refers to a base wherein the cation is $Na^+$.

The expression "water-miscible organic solvent," unless otherwise indicated, refers to an organic solvent which is soluble in water in all proportions at standard temperature and pressure. Suitable water-miscible organic solvents include, for example, methanol, ethanol, isopropanol, acetone, acetonitrile, tetrahydrofuran, dioxane, dimethyl formamide, dimethylacetamide, and N-methylpyrrolidinone.

The term "co-precipitation", used herein refers to simultaneous precipitation of more than one dissolved substance from a solution or suspension.

The expressions, "aqueous medium" and "aqueous solvent" refer, unless otherwise indicated, to a solvent or medium that is water, or a mixture of water and one or more water-miscible organic solvents.

The expression "sodium gluconate," as used herein, refers to the sodium salt of D-gluconic acid. The expression "sodium gluconate" may refer to preformed sodium gluconate. Alternately, "sodium gluconate" may refer to sodium gluconate formed in situ by combination of gluconic acid and a sodium base such as sodium hydroxide or sodium carbonate that serves to form a mixture containing sodium cations and gluconic acid anions.

The expression "substantially free of crystalline material" refers, unless otherwise indicated, to a material that is indistinguishable via X-ray powder diffraction from the same material present as exclusively an amorphous solid.

The expression "solid dosage form" means a solid pharmaceutical preparation in the form of, for example a tablet, capsule, pill, powder, or granule.

DETAILED DESCRIPTION OF THE INVENTION

Figure 1:
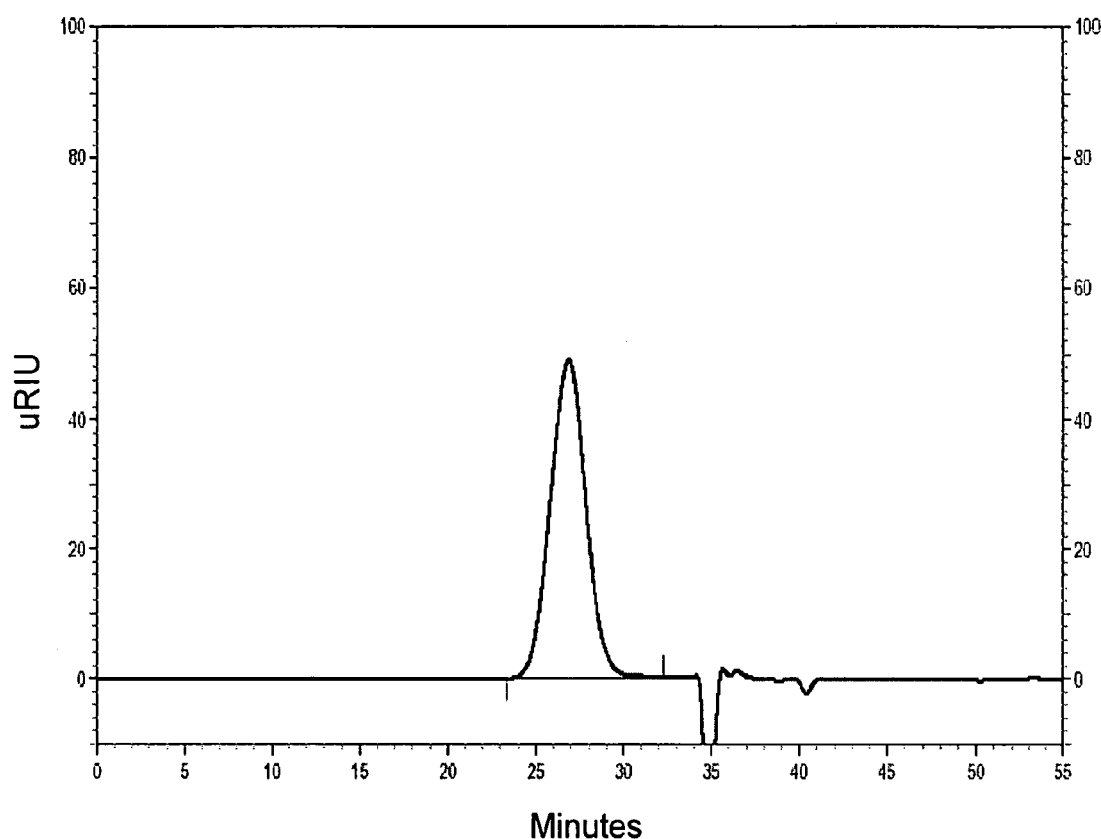
FIG. 1 shows a GPC trace of sodium ferric gluconate complex prepared by the process of the invention, having a weight average molecular weight of 47,000 Daltons.

Sodium ferric gluconate complexes presently employed in therapy contain significant amounts of contaminants detectable by GPC analysis. The present invention provides a process for the preparation of sodium ferric gluconate complexes that are substantially free of excipients. The sodium ferric gluconate complexes, substantially free of excipients, can be used to formulate a therapeutic sodium ferric gluconate complex in sucrose composition containing lower levels of contaminants.

A. Ferric Hydroxide

The term "ferric hydroxide" as employed herein, includes the various forms of ferric hydroxide, including, for example, hydrated ferric oxide, ferric oxy hydroxide, polymeric ferric hydroxide, ferric hydroxide gel, partially neutralized ferric salts and partially neutralized polymeric ferric salts. The various forms of ferric hydroxide may be expressed according to Formula I:

$$\{(Fe^{III})_a[Y]_k[X/e]_m[O]_b[H]_d\}_z \qquad \text{I}$$

wherein "a" and "z" represent integers that are independently 1 to about 1000, preferably 1 to about 500; "Y" is a cation other than $Fe^{III}$, for example, ammonium or alkyl ammonium; "b," "d," "k" and "m" represent integers that are independently 0 to about 1000, preferably 0 to about 500; "X" is an anion, for example, chloride, bromide, iodide, nitrate, sulfate, acetate, citrate, and other acid anions; "e" represents the equivalent number of the anion X.

B. Preparation of Ferric Hydroxide

The ferric hydroxide utilized as the starting material in the process of the present invention may be prepared by reacting a ferric salt with at least about one molar equivalent of a base, based on the amount of the ferric salt. A mixture of ferric salts, and/or a mixture of bases, may be employed. Suitable ferric salts include, for example, ferric chloride, ferric nitrate and mixtures thereof.

Suitable bases for reaction with the ferric salt include, for example, alkali metal carbonates, alkali metal bicarbonates, alkali metal hydroxides, water-soluble amines and mixtures thereof. Preferred bases include sodium carbonate, sodium bicarbonate, sodium hydroxide, tris-hydroxymethyl-aminoethane and mixtures thereof.

The ferric hydroxide may be prepared by (a) providing a reaction mixture comprising a ferric salt dissolved in an aqueous medium; (b) adding to the reaction mixture a first base in an amount from about 1 to about 2 equivalents based on the amount of ferric salt; (c) allowing the reaction mixture to equilibrate for a time interval that is greater than about 10 minutes, preferably in the range of from about 10 to about 120 minutes, more preferably, in the range of from about 10 to about 60 minutes; (d) adding to the equilibrated reaction mixture a second base in an amount sufficient to adjust the pH of the reaction mixture to a selected pH; and (e) collecting the ferric hydroxide from the reaction mixture.

The first and second bases may be the same, or may be different bases. The bases may be added to the reaction mixture in solution or suspension in an aqueous solvent. Alternately the bases may be added neat, i.e., a base such as sodium carbonate may be added as a dry solid.

The first base may be added to the reaction mixture batchwise, i.e., all at once, or continuously or semi-continuously over a time interval at a constant or variable addition rate. A slow continuous addition may be performed as a titration wherein the pH of the mixture is continuously monitored, preferably using a pH meter. The addition of the base may be stopped when a selected pH, preferably in the range from about 2.0 to about 2.5, is achieved in the reaction mixture. The addition rate of the base for slow continuous addition is preferably from about 0.02 to about 0.2 equivalents of the base per minute, based on the amount of the ferric salt in the reaction mixture.

After the addition of the first base to the reaction mixture, the reaction mixture is allowed to equilibrate, with or without stirring. The temperature is preferably maintained in the range from about 20° C. to about 30° C. The pH of the reaction mixture is typically observed to drop to a pH in the range from about 1.4 to about 1.8 during the time interval when the reaction mixture is allowed to equilibrate.

The second base is preferably added to the reaction mixture continuously at a constant addition rate while the pH of the resulting mixture is monitored. Suitable addition rates are from about 0.02 to about 0.2 equivalents of the base per minute, based on the amount of the ferric salt in the reaction mixture.

The addition of the second base to the reaction mixture is continued until the pH of the reaction mixture is in the range from about 3.5 to about 9. According to some embodiments, the desired pH is about 4. According to other embodiments, the desired pH is about 7. According to still other embodiments, the desired pH is about 8.3. Ferric hydroxide forms as a precipitate in the reaction mixture during the second base addition. The ferric hydroxide precipitate begins to form at a pH of about 3.

Following complete addition of the second base, the reaction mixture, comprising a suspension of ferric hydroxide, is allowed to equilibrate for a time interval from about 5 minutes to about 60 minutes. The ferric hydroxide precipitate is observed to settle during the equilibration period.

The ferric hydroxide precipitate may be collected from the reaction mixture by any suitable method, including, for example, filtration, centrifugation, or decanting. Filtration is preferred. Suitable filtration methods include vacuum filtration, for example through a Buchner funnel. (for filtrations on the scale of manufacturing operations an agitated nutsch filter is preferred). The resulting filter cake comprising ferric hydroxide is washed with water and then prepared as a slurry in an aqueous solvent. Suitable aqueous solvents include water and mixtures of water with one or more water-miscible organic solvents, wherein the water-miscible organic solvent comprises up to about 30% of the aqueous solvent.

C. Preparation of Sodium Ferric Gluconate

To prepare sodium ferric gluconate, a suspension or a slurry of ferric hydroxide, as prepared above, is reacted with sodium gluconate and a sodium base in a reaction mixture comprising an aqueous medium. The molar ratio of ferric hydroxide to sodium gluconate is preferably in the range from about 0.2:1 to about 5:1 of sodium gluconate to ferric hydroxide, more preferably in the range from about 1:1 to about 5:1 of sodium gluconate to ferric hydroxide, preferably from about 1:1 to about 3:1. The mixture of the ferric hydroxide and sodium gluconate is made basic by the addition of the sodium base. The sodium base is preferably aqueous sodium hydroxide or aqueous sodium carbonate or a mixture thereof.

The sodium base is preferably added in an amount sufficient to obtain the selected pH of the aqueous reaction mixture. According to some embodiments of the invention, the ratio of sodium base to ferric hydroxide added to the aqueous reaction mixture is preferably from about 1:1 to about 1:10, more preferably about 1:5 on a mol/mol basis.

The sodium base may be added to the aqueous medium, and the ferric hydroxide may subsequently be added. Alternately, the sodium base may be added to the mixture of the ferric hydroxide and sodium gluconate in the aqueous medium.

The reaction mixture is optionally cooled to a temperature in the range from about 20° C. to about 30° C., prior to the step of isolating sodium ferric gluconate complex from the reaction mixture.

The reaction of ferric hydroxide and sodium gluconate may be optionally monitored to determine the weight average molecular weight and purity of the sodium ferric gluconate complex product. Monitoring may be done by removing an aliquot of the reaction mixture and conducting a molecular weight analysis on the aliquot.

When the reaction of ferric hydroxide and sodium gluconate is complete (as determined by observation of the clarity of the reaction mixture and by GPC analysis of reaction aliquots), the sodium ferric gluconate complex is isolated from the mixture. Isolation is achieved by adding one or more water-miscible organic solvents to the reaction mixture to precipitate the sodium ferric gluconate complex. The amount of water-miscible organic solvent added to the reaction mixture is preferably in the range of from about 1 to about 10 times the volume of the reaction mixture to which it is added. The product sodium ferric gluconate complex that precipitates from the reaction mixture after addition of the water-miscible organic solvent is collected from the reaction mixture. Suitable methods for collecting the product include, for example, filtration, centrifugation and decanting. The product is preferably collected by filtration. The selection of suitable filtration media, for example, a sintered glass funnel or Buchner funnel, is within the capability of one of ordinary skill in the art.

The product sodium ferric gluconate complex thus collected, as described above, may be optionally purified by (a) dissolving the isolated sodium ferric gluconate complex in an aqueous solvent; (b) forming a mixture by adding at least one water-miscible organic solvent to the solution formed in step (a), the solvent being added in an amount sufficient to precipitate sodium ferric gluconate complex from the mixture formed in step (b); and (c) collecting the precipitated purified sodium ferric gluconate complex.

The aqueous solvent used to dissolve the isolated sodium ferric gluconate complex is preferably employed in an amount in the range from about 1 to about 7 times the weight of the filtrate or residue to be dissolved therein. The pH of the resulting solution is preferably adjusted to a pH in the range from about 7.5 to about 14, more preferably from about 8 to about 14, more preferably from about 8 to about 12, by the addition of a base such as sodium hydroxide. Suitable water-miscible organic solvents for the precipitation of purified sodium ferric gluconate complex include, for example, methanol, ethanol, acetone, tetrahydrofuran, dioxane, acetonitrile and mixtures thereof. The amount of the water-miscible organic solvent added to the solution of the residue or filtrate to precipitate sodium ferric gluconate complex is preferably in the range from a 1:1 to a 1:7 ratio of the water-miscible organic solvent to aqueous solvent.

Suitable methods for collecting the precipitated purified sodium ferric gluconate complex include, for example, filtration, centrifugation and decanting. The purified product is preferably collected by filtration.

The purified sodium ferric gluconate complex thus obtained, is optionally dried. Drying of the purified sodium ferric gluconate complex may be carried out under vacuum or at atmospheric pressure, in air or under an inert atmosphere such as, for example, nitrogen. Preferably the purified product is dried at a temperature from about 25° C. to about 140° C., more preferably from about 25° C. to about 110° C.

The purified sodium ferric gluconate complex prepared according to the process of the invention preferably contains no more than about 2% wt/wt or lower of free gluconate. The purified complex preferably contains no more than about 5% wt/wt water and solvents.

The thus-obtained precipitated purified sodium ferric gluconate complex, may be formulated as a parenteral iron formulation. One example of a parenteral iron formulation comprises dissolving the precipitated purified sodium ferric gluconate complex, containing from about 20% to about 50% ferric iron, in an aqueous sucrose solution, preferably about 20% aqueous sucrose, to form a parenteral iron formulation. The concentration of precipitated purified sodium ferric gluconate complex in the sucrose solution is selected such that the composition is suitable as an injectable form of ferric iron. Another example of a parenteral iron formulation comprises dissolving the precipitated purified sodium ferric gluconate complex, containing from about 2% to about 15% ferric iron, in water for injection to form a parenteral iron formulation. The concentration of sodium ferric gluconate complex in the aqueous solution is selected such that the composition is suitable as an injectable form of ferric iron.

According to another embodiment of the invention, there is provided a pharmaceutical composition in solid dosage form comprising a pharmaceutically acceptable carrier and a sodium ferric gluconate complex having a molecular weight in the range from about 20,000 to about 700,000 Daltons. The pharmaceutical composition of the invention may be formulated for oral administration and may be in the form of a tablet, capsule, pill, powder, granule or other suitable solid dosage form with suitable excipients and additives.

For example, the sodium ferric gluconate complex formed by the process of the present invention may be combined with at least one excipient such as a filler, binder, humectant, disintegrating agent, solution retarder, absorption accelerator, wetting agent absorbent or lubricating agent. According to one embodiment of a solid dosage form of a sodium ferric gluconate complex of the invention, the active agent may be combined with carboxymethylcellulose calcium, magnesium stearate, mannitol and starch, and then formed into tablets by conventional tableting methods.

The pharmaceutical composition according the invention comprises a sodium ferric gluconate complex that contains from about 1 to about 55% ferric iron by weight, preferably from about 1 to about 50% ferric iron by weight, more preferably from about 30 to about 50% ferric iron by weight.

The pharmaceutical composition according the invention preferably contains from about 5 to about 200 mg of ferric iron, more preferably from about 10 to about 150 mg, most preferably from about 25 to about 100 mg.

The practice of the invention is illustrated by the following non-limiting examples.

EXAMPLES

The following analytical methods are employed in the Examples that follow.

Molecular Weight Determination for Sodium Ferric Gluconate Complex

GPC analyses were performed using a Shimadzu Class VP, SCL10A-VP, with an LC10AD pump, equipped with a refractive index detector (Shimadzu RID 10A). The mobile phase employed was an aqueous buffer prepared by dissolving 7.12 g of dibasic sodium phosphate dehydrate, 5.52 g of monobasic sodium phosphate, and 0.40 g of sodium azide in 2 liters of water.

The separation media consists of two 7.8-mm×30-cm columns (Waters Ultrahydrogel GPC column containing packing L39, with pore sizes of 1000 Å and 120 Å, respectively) set up in series. The column temperatures were maintained at 45° C.±2° C. and the flow rate was about 0.5 mL per minute.

Standard solutions (Waters Dextran molecular weight standard kit part # WAT 054392) were prepared by accurately weighing about 20 mg of each polysaccharide molecular weight standard (5,000–400,000 Da) into separate 5-mL volumetric flasks. Mobile phase (about 4 mL) was added to each flask and the resulting mixture was allowed to stand at or below 25° C. for a minimum of 12 hours. After the agglomerate particles of each standard solution swelled to their fullest extent, each standard solution was gently agitated until the polysaccharide dissolved. Chromatograms of freshly prepared standard solutions regularly show a small, unidentified secondary peak following the main peak. Any standard solutions wherein the secondary peak reached half the height of the main peak were discarded.

A system suitability test solution was also prepared by dissolving 200 mg of high molecular weight dextran and 100 mg of glucose in 20 mL of the mobile phase.

Test sample solutions of sodium ferric gluconate complex for analysis were prepared by transferring about 200 mg of each sodium ferric gluconate complex to a 10-mL volumetric flask, diluting to the line with mobile phase, and mixing. Test samples which were reaction aliquots were prepared by diluting 1 mL of the reaction mixture to 10 mL with mobile phase.

About 25 μL of each standard solution and test sample solution was injected (Shimadzu auto injector SIL10A-VP) onto the column. Chromatograms were recorded and the retention times and peak areas of all components above the detectability threshold were measured. The analyte retention times were as follows:

| Sodium Ferric Gluconate complex peak | About 27 minutes |
| Gluconate (free) peak | About 35 minutes |
| Sucrose (free) peak | About 38 minutes |

The retention times of the standard solutions and their molecular weights were plotted to generate a third order (cubic) calibration curve. The correlation coefficient obtained was not less than 0.98. The molecular weight of the complex was calculated using the calibration curve. The molecular weight distribution curve of the each sample was sliced into fractions. The weight-average molecular weight (Mw) was calculated according to the formula:

$$\sum (A_T M_T) / \sum A_T$$

wherein $A_T$ is the area of each fraction of the sample distribution; and MT is the corresponding mean molecular weight of each fraction as determined from its retention time on the calibration curve.

Determination of Iron Content by Atomic Absorption Spectroscopy (AAS)

An iron content calibration curve was prepared by plotting absorbances at the iron emission line at 248.3 nm versus concentration (μg per mL) for a series of standard iron solutions. The absorbances were measured with a Perkin Elmer 5000 atomic absorption spectrophotometer equipped with an iron hollow-cathode lamp and air-acetylene flame, and using a calcium chloride solution as a blank. Reaction aliquots from reactions performed in the preparation of the sodium ferric gluconate complexes of the invention were dissolved in water, and the absorbance at 248.3 nm were recorded. The content of iron in the samples prepared from reaction aliquots was determined according to the prepared calibration curve.

Fourier Transform Infrared (FTIR) Analyses of Sodium Ferric Gluconate Complex:

About 50 mg of sodium ferric gluconate complex was finely crushed using an agate pestle and mortar. The crushed sample was placed over the trough plate of the Horizontal Attenuated Total Reflectance (HATR) assembly of a Perkin Elmer Spectrum 1 FTIR Spectrometer. The spectrum was recorded (4 scans, 4000 to 800 cm$^{-1}$) and corrected for background signal.

NMR Analyses of Sodium Ferric Gluconate Complex:

About 5 mg of sodium ferric gluconate complex was dissolved in 1.5 mL of $D_2O$ and transferred into an NMR sample tube. The proton NMR was recorded (−5 to 20 ppm, Varian 400 MHz NMR spectrometer) using standard parameters with 3-trimethylsilylpropionic acid sodium salt (TSP) as an internal standard.

Determination of Degree of Crystallinity of Sodium Ferric Gluconate Complexes by X-ray Powder Diffraction Analyses X-ray powder diffraction analyses were performed on the dried purified products of the reactions performed in the preparation of the sodium ferric gluconate complexes of the invention. Each sample of sodium ferric gluconate complex of the invention was analyzed as a fine powder. The dried purified reaction products required no additional processing before X-ray diffraction analysis. The powder sample to be analyzed was placed onto a zero background holder and inserted into a Philips PW1800 XR diffractometer. The X-ray analysis comprised Cu radiation over the angular range (theta) of 5° to 60° with a step size of 0.03°. The analyses at each step required from about 5 to about 30 seconds depending on the degree of crystallinity of the sample.

Example 1

Preparation of Sodium Ferric Gluconate Complex

Step 1—Preparation of Ferric Hydroxide

Ferric chloride hexahydrate (5 g, 18.5 mmol) was dissolved in deionized water (20 mL) at a temperature of about 20° C. To the stirred ferric chloride solution was added sodium carbonate 30% w/v aqueous solution dropwise with the pH of the ferric chloride solution monitored during the addition (first base addition). The addition was stopped when the pH reached 2.2. The pH of the mixture was monitored using a pH meter. The temperature of the mixture was maintained at about 20° C. Following the addition of sodium carbonate, the resulting mixture was dark brown to reddish brown in color. The mixture was allowed to stand for about 30 min., during which time the pH of the reaction mixture was observed to drop to 1.7. Additional sodium carbonate solution (second base addition) was added as the pH of the mixture was monitored. A gelatinous precipitate appeared at a pH of about 3.0. The addition of the sodium carbonate solution was continued until the pH of the mixture reached 4.0, yielding a suspension of ferric hydroxide. Following the addition of sodium carbonate solution, the reaction mixture was allowed to stand for about 10 minutes to allow the precipitate to settle. The precipitated ferric hydroxide was then collected by filtration and washed with water (25 mL). The wet filter cake (about 15 g) was made into a slurry in water (about 20 mL).

Step 2—Preparation of the Sodium Ferric Gluconate Complex

To a 100 mL three necked round bottom flask, fitted with reflux condenser and stirrer assembly, was added water (20 mL) and sodium gluconate (12 g). The resulting mixture was heated in an oil bath maintained at 120° C. for about 10 min. The temperature of the mixture reached about 100–105° C. Sodium hydroxide (about 2 mL, 20% w/v) was added to the heated reaction mixture. Then the slurry of ferric hydroxide prepared in Step 1 was added to the sodium gluconate mixture over about 15 min. The reaction mixture formed a clear dark brown solution after the addition of the suspension of ferric hydroxide was completed. Following the addition of the ferric hydroxide slurry, the temperature of the reaction mixture was maintained at about 100 to 105° C. for about 2 hrs. The reaction mixture was subsequently cooled to ambient temperature (20 to 25° C.). An aliquot (1 mL) of the reaction mixture was removed for GPC analysis to confirm the weight average molecular weight of the product sodium ferric gluconate complex (about 45,000 Daltons).

Step 3—Isolation of the Sodium Ferric Gluconate Complex

Figure 3:
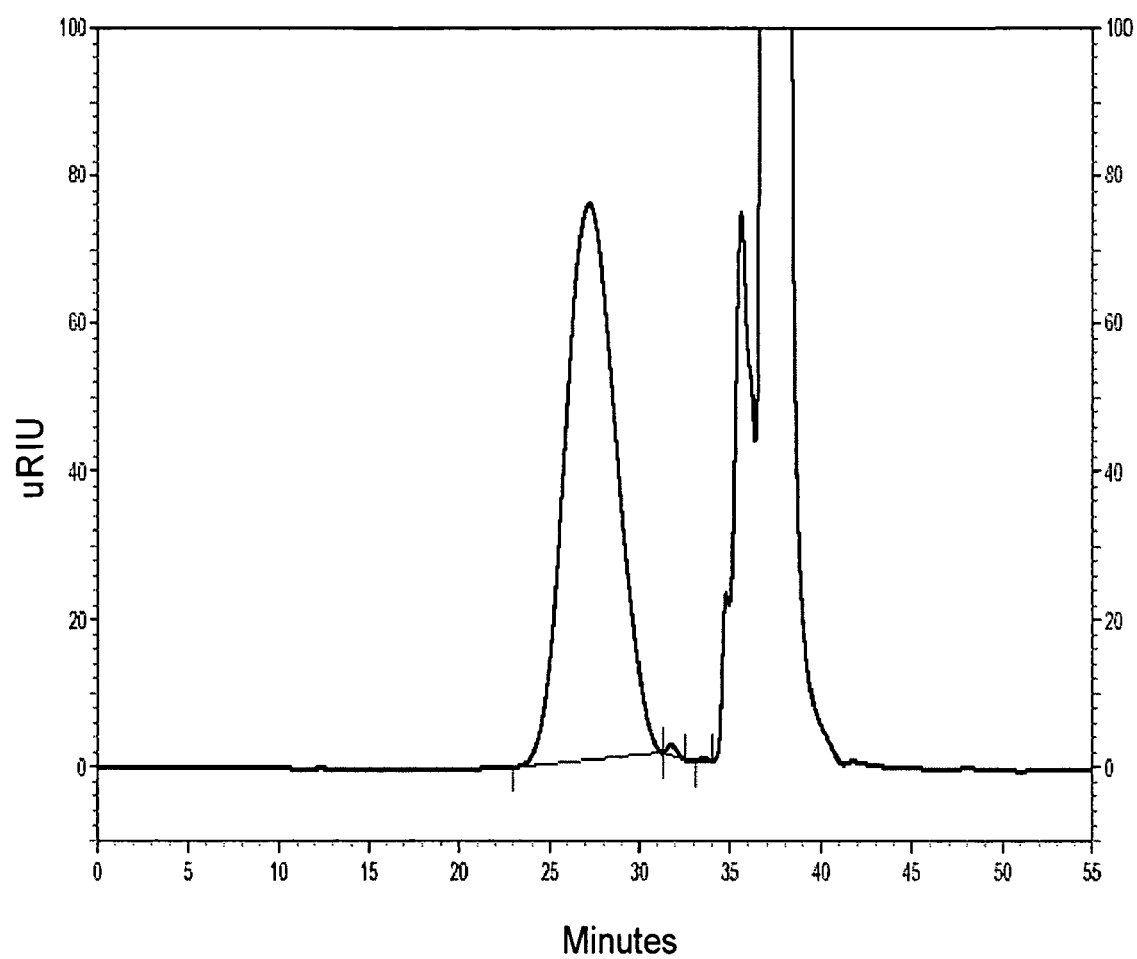
FIG. 3 shows a GPC trace of FERRLECIT® brand sodium ferric gluconate complex in sucrose.

A water-miscible organic solvent (ethanol, about 300 mL) was added to the reaction mixture formed in Step 2, at about 25° C. with stirring. A dark brown precipitate formed and was collected by filtration. The collected product was further purified by dissolving it in water (10 mL) and subsequently adding ethanol (50 mL) to the dissolved product to precipitate a purified product. The precipitate was collected by filtration, washed with ethanol, and dried under vacuum at about 50° C. The purified product was identified as sodium ferric gluconate complex and was analyzed by GPC. The GPC analysis showed that the complex corresponding to the principle peak was present in greater than 95% purity and that the weight average molecular weight remained at about 45,000 Daltons. This peak corresponds to the sodium ferric gluconate peak obtained on analysis of the marketed sodium ferric gluconate in sucrose (FERRLECIT®), shown in FIG. 3. The molecular weight and weight average molecular weight values were determined using calibration curves and third order fitting.

Figure 5:
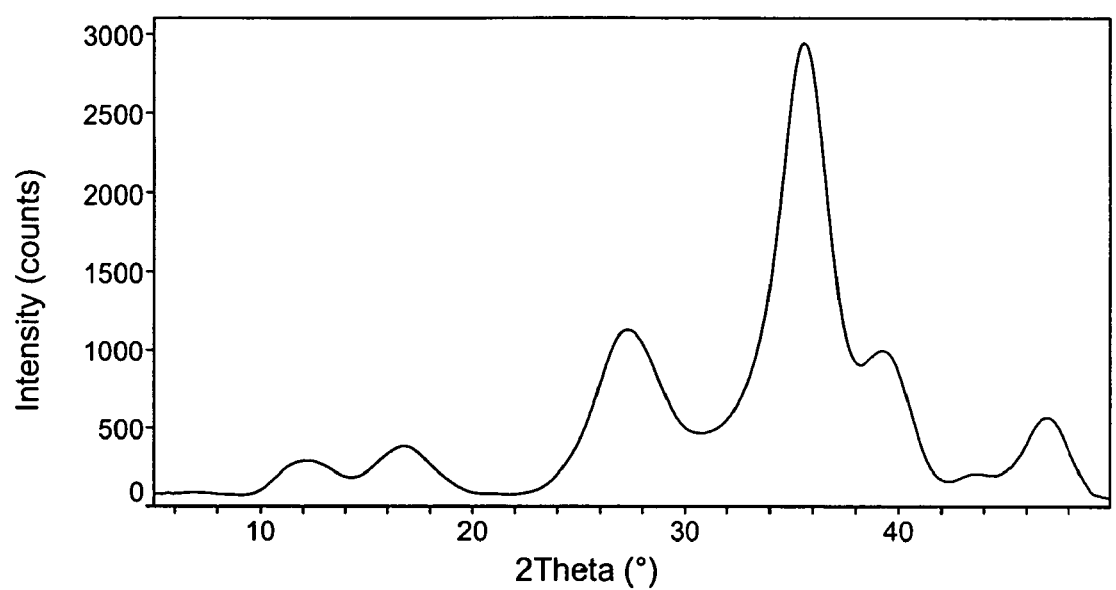
FIG. 5 shows an X-ray diffractogram of a dried, purified ferric gluconate complex prepared in Example 1 which is amorphous and substantially free of crystalline sodium ferric gluconate complex.

Powder diffraction analysis was obtained for a sample of the dried purified product. The powder diffraction analysis is reproduced in FIG. 5. The powder diffraction analysis indicates the presence of an amorphous product which is substantially free of crystalline sodium ferric gluconate complex.

Example 2

Preparation of Sodium Ferric Gluconate Complex

The procedure of Example 1 was followed, except that the ferric salt used in Step 1 was ferric nitrate nonahydrate (7.5 g, 18.5 mmol).

Figure 4:
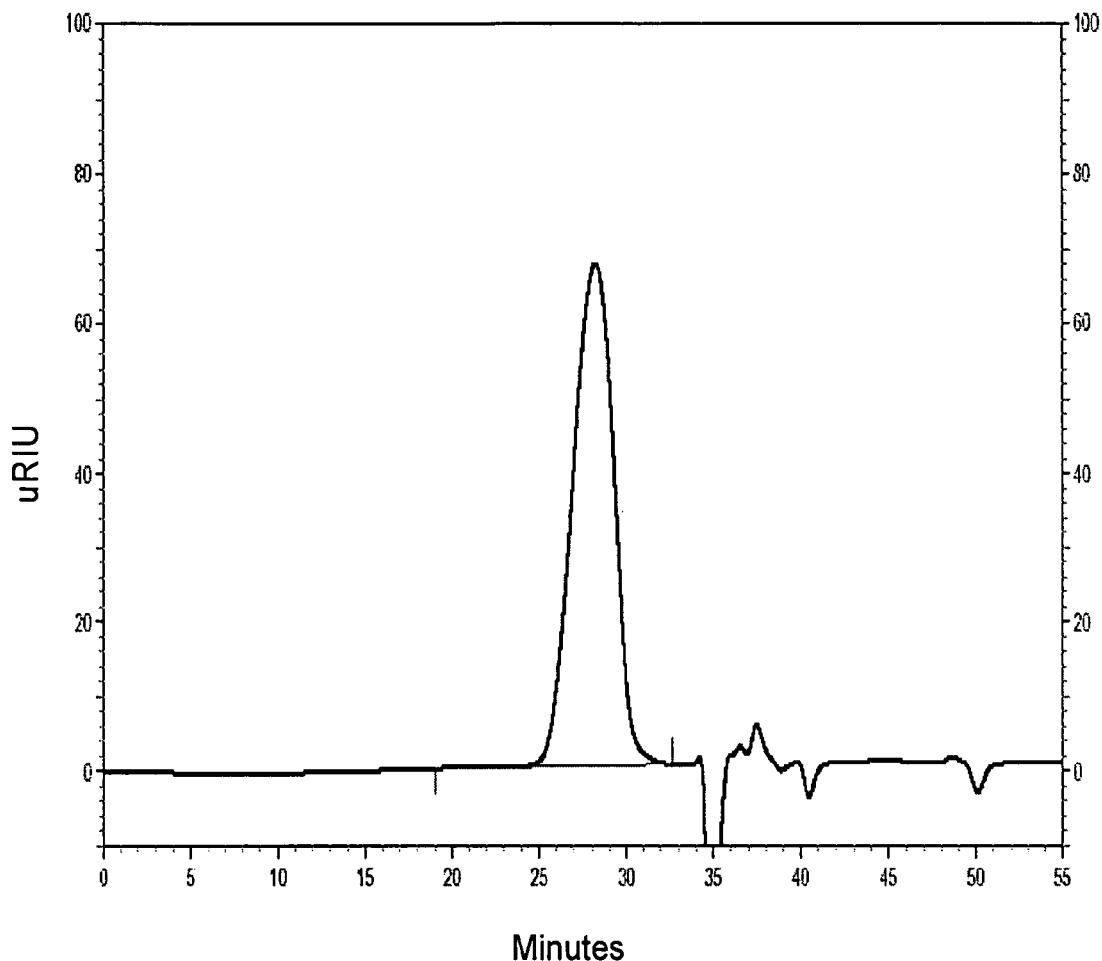
FIG. 4 shows a GPC trace of sodium ferric gluconate complex in 20% aqueous sucrose, prepared by the process of the invention, wherein the sodium ferric gluconate complex has a weight average molecular weight of 50,000 Daltons.

The GPC analyses of the reaction aliquot and of the final purified and dried product indicated that the complex corresponding to the principle peak was present in greater than 95% purity and that the weight average molecular weight was about 25,000 Daltons. The GPC analysis of the purified product is shown in FIG. 4.

Example 3

Preparation of Sodium Ferric Gluconate Complex

The procedure of Example 1 was followed, except that the second base addition was continued until the pH reached 7.0.

The GPC analyses of the reaction aliquot and of the final purified and dried product indicated that the complex corresponding to the principle peak was present in greater than 95% purity and that the weight average molecular weight was about 47,000 Daltons. The GPC analysis of the purified product is shown in FIG. 1. This peak corresponds to the sodium ferric gluconate peak obtained on analysis of the marketed sodium ferric gluconate in sucrose (FERRLECIT®), shown in FIG. 3.

Example 4

Preparation of Sodium Ferric Gluconate Complex

The procedure of Example 1 was followed, except that the second base addition was continued until the pH reached 8.3.

The GPC analyses of the reaction aliquot and of the final purified and dried product indicated that the complex corresponding to the principle peak was present in greater than 95% purity and that the weight average molecular weight was about 50,000 Daltons.

Example 5

Preparation of Sodium Ferric Gluconate Complex

The procedure of Example 1 was followed, except that in Step 2, the 20% sodium hydroxide solution (2 mL) was added after the completion of the addition of the slurry of ferric hydroxide.

The GPC analyses of the reaction aliquot and of the final purified and dried product indicated that the complex corresponding to the principle peak was present in greater than 95% purity and that the weight average molecular weight was about 80,000 Daltons.

Example 6

Preparation of Sodium Ferric Gluconate Complex

The procedure of Example 1 was followed, except that the first base addition comprised addition of the base (sodium carbonate 30% w/v aqueous solution) as a single portion of 3.3 mL (about 1 equivalent based on the amount of ferric salt).

The GPC analyses of the reaction aliquot and of the final purified and dried product indicated that the complex corresponding to the principle peak was present in greater than 95% purity and that the weight average molecular weight was about 80,000 Daltons.

Example 7

Preparation of Sodium Ferric Gluconate Complex

The procedure of Example 1 was followed, except that the first base addition comprised batchwise addition of the base (sodium carbonate 30% w/v aqueous solution) in a single portion of 6.6 mL (about 2 equivalents based on the amount of ferric salt).

The GPC analyses of the reaction aliquot and of the final purified and dried product indicated that the complex corresponding to the principle peak was present in greater than 95% purity and that the weight average molecular weight was about 45,000 Daltons.

Example 8

Preparation of Sodium Ferric Gluconate Complex

The procedure of Example 7 was followed, except that the second base addition was continued until the pH reached 7.0.

The GPC analyses of the reaction aliquot and of the final purified and dried product indicated that the complex corresponding to the principle peak was present in greater than 95% purity and that the weight average molecular weight was about 45,000 Daltons.

Example 9

Preparation of Sodium Ferric Gluconate Complex and Analysis of Variation in Weight Average Molecular Weight Over Time The procedure of Example 8 was followed, except for the following changes in Steps 1 and 2.

Step 1: The amount of the first base addition was 3.3 mL of 30% wt./Vol, aqueous sodium carbonate.

Step 2: One aliquot of the reaction mixture was removed immediately following completion of the addition of the ferric hydroxide slurry. The reaction mixture was then maintained at 100° C. to 105 20 C. for about three hours, and then cooled to ambient temperature (20° C. to 25° C.). A second aliquot of the reaction mixture was removed. GPC analysis was performed on both the first and second aliquots. The weight average molecular weight determined for the first aliquot was about 100,000 Daltons. The weight average molecular weight determined for the second aliquot was about 45,000 Daltons. The GPC analyses of the final purified and dried product indicated a weight average molecular weight of about 45,000 Daltons.

Example 10

Preparation of Sodium Ferric Gluconate Complex

The procedure of Example 8 was followed, except for the following changes in Steps 1 and 2.

Step 1: The amount of the first base addition was 3.3 mL of 30% wt./Vol, aqueous sodium carbonate.

Step 2: The water-miscible organic solvent used to precipitate the complex and to precipitate the purified complex was methanol (350 mL and 50 mL, respectively).

The GPC analyses of the reaction aliquot and of the final purified and dried product indicated that the complex corresponding to the principle peak was present in greater than 95% purity and that the weight average molecular weight was about 55,000 Daltons.

Example 11

Preparation of Sodium Ferric Gluconate Complex

The procedure off Example 8 was followed except the amount of the first base addition in Step 1 was 3.3 mL of 30% wt./Vol, aqueous sodium carbonate, and the water-miscible organic solvent used to precipitate the complex and the purified complex in Step 2 was isopropanol (350 mL and 50 mL, respectively).

The GPC analyses of the reaction aliquot and of the final purified and dried product indicated that the complex corresponding to the principle peak was present in greater than 95% purity and that the weight average molecular weight was about 50,000 Daltons.

Example 12

Preparation of Sodium Ferric Gluconate Complex

The procedure of Example 8 was followed, except the amount of the first base addition in Step 1 was 3.3 mL of 30% wt./Vol, aqueous sodium carbonate, and the water-miscible organic solvent used to precipitate the complex and in Step 2 was acetone (350 mL).

The GPC analyses of the reaction aliquot and of the final purified and dried product indicated that the complex corresponding to the principle peak was present in greater than 95% purity and that the weight average molecular weight was about 50,000 Daltons.

Figure 6:
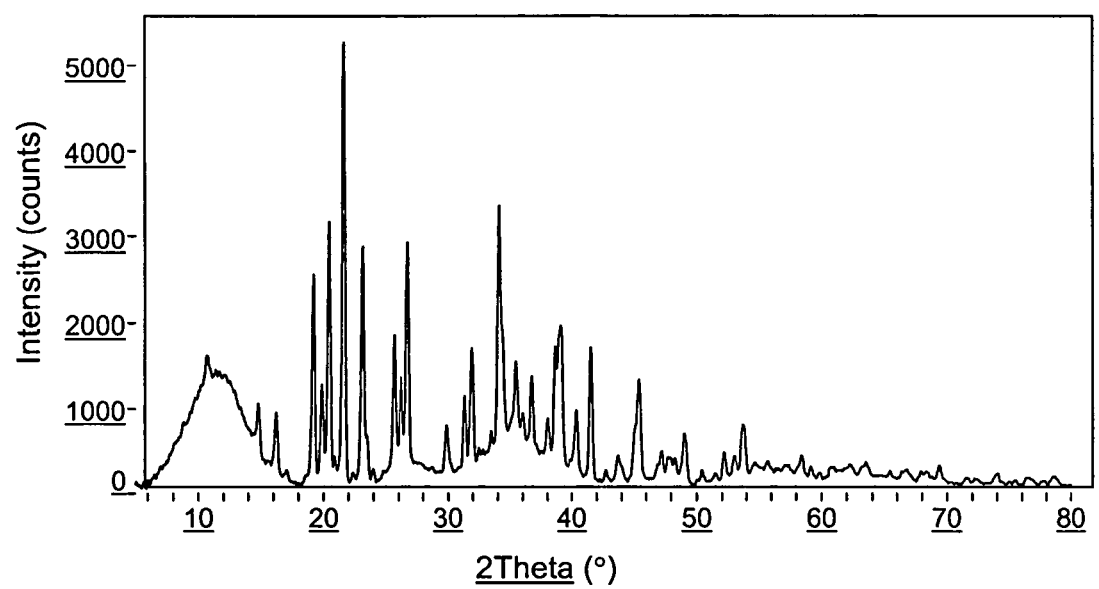
FIG. 6 shows an X-ray diffractogram of a dried, purified ferric gluconate complex prepared in Example 27 which contains a detectable amount of crystalline sodium ferric gluconate complex.

Powder diffraction analysis was obtained for a sample of the dried purified product. The powder diffraction analysis is reproduced in FIG. 6. The powder diffraction analysis indicates the presence of a product which contains a significant amount of crystalline sodium ferric gluconate complex.

Example 13

Preparation of Sodium Ferric Gluconate Complex

The procedure of Example 8, except the amount of the first base addition in Step 1 was 3.3 mL of 30% wt./Vol, aqueous sodium carbonate, and the water-miscible organic solvent used to precipitate the complex in Step 2 was acetonitrile (300 mL).

The GPC analyses of the reaction aliquot and of the final purified and dried product indicated that the complex corresponding to the principle peak was present in greater than 95% purity and that the weight average molecular weight was about 65,000 Daltons.

Example 14

Preparation of Sodium Ferric Gluconate Complex

The procedure of Example 8 was followed, except the amount of the first base addition in Step 1 was 3.3 mL of 30% wt./Vol, aqueous sodium carbonate, and the purified product was dried under vacuum at a temperature of 120° C.

The GPC analyses of the reaction aliquot and of the final purified and dried product indicated that the complex corresponding to the principle peak was present in greater than 95% purity and that the weight average molecular weight was about 50,000 Daltons.

Example 15

Preparation of Sodium Ferric Gluconate Complex

The procedure of Example 8 was followed, except the amount of the first base addition in Step 1 was 3.3 mL of 30% wt./Vol, aqueous sodium carbonate, and the amount of sodium gluconate used in Step 2 was 8 g.

The GPC analyses of the reaction aliquot and of the final purified and dried product indicated that the complex corresponding to the principle peak was present in greater than 95% purity and that the weight average molecular weight was about 50,000 Daltons.

Example 16

Preparation of Sodium Ferric Gluconate Complex

The procedure of Example 8 was followed, except the first base addition in Step 1 was the addition of 1 g of sodium carbonate added as a solid.

The GPC analyses of the reaction aliquot and of the final purified and dried product indicated that the complex corresponding to the principle peak was present in greater than 95% purity and that the weight average molecular weight was about 50,000 Daltons.

Example 17

Preparation of Sodium Ferric Gluconate Complex

The procedure of Example 8 was followed, except the first base addition in Step 1 was solid sodium bicarbonate (first addition was 1.6 g added all at once).

The GPC analyses of the reaction aliquot and of the final purified and dried product indicated that the complex corresponding to the principle peak was present in greater than 95% purity and that the weight average molecular weight was about 50,000 Daltons.

Example 18

Preparation of Sodium Ferric Gluconate Complex

The procedure of Example 8 was followed, except the first added base in Step 1 was solid sodium bicarbonate (first addition was 1.6 g added all at once), and the second added base was sodium hydroxide (20% aqueous solution).

The GPC analyses of the reaction aliquot and of the final purified and dried product indicated that the complex corresponding to the principle peak was present in greater than 95% purity and that the weight average molecular weight was about 65,000 Daltons.

Example 19

Preparation of Sodium Ferric Gluconate Complex

The procedure of Example 8 was followed, except that the first added base in Step 1 was tris-hydroxyethylaminomethane (first addition is 2.2 g added all at once), and the second added base was sodium hydroxide (20% aqueous solution).

The GPC analyses of the reaction aliquot and of the final purified and dried product indicated that the complex corresponding to the principle peak was present in greater than 95% purity and that the weight average molecular weight was about 50,000 Daltons.

Example 20

Preparation of Sodium Ferric Gluconate Complex

The procedure of Example 8 was followed, except the amount of the first base addition in Step 1 was 3.3 mL of 30% wt./Vol, aqueous sodium carbonate, and the heating temperature in Step 2 was 80° C.

The GPC analyses of the reaction aliquot and of the final purified and dried product indicated that the complex corresponding to the principle peak was present in greater than 95% purity and that the weight average molecular weight was about 50,000 Daltons.

Example 21

Preparation of Sodium Ferric Gluconate Complex

The procedure of Example 8 was followed, except the amount of the first base addition in Step 1 was 3.3 mL of 30% wt./Vol, aqueous sodium carbonate, and the solvent in Step 2 was 20 mL of water and 5 mL of ethanol.

The GPC analyses of the reaction aliquot and of the final purified and dried product indicated that the complex corresponding to the principle peak was present in greater than 95% purity and that the weight average molecular weight was about 50,000 Daltons.

Example 22

Preparation of Sodium Ferric Gluconate Complex

The procedure of Example 8 was followed, except the amount of the first base addition in Step 1 was 3.3 mL of 30% wt./Vol, aqueous sodium carbonate.

Also in Step 3, the purification was carried out by dissolving the product in a 40% wt./Vol. sucrose solution in water (10 mL) and subsequently adding ethanol (50 mL) to the dissolved product to precipitate a purified product. The precipitate was collected by filtration, washed with ethanol, and dried under vacuum at about 50° C.

The purified product was identified as sodium ferric gluconate complex co-precipitated with sucrose and was analyzed by GPC. The GPC analysis showed that the complex corresponding to the principle peak was present in greater than 95% purity and that the weight average molecular weight remained at about 50,000 Daltons.

Example 23

Preparation of Sodium Ferric Gluconate Complex

The procedure of Example 8 was followed, except the amount of the first base addition in Step 1 was 3.3 mL of 30% wt./Vol, aqueous sodium carbonate, and 5 g of sodium nitrate was added to the reaction mixture prior to the addition of any base.

Also, in Step 3, the purification was carried out by dissolving the collected product in a 20% wt./Vol. sodium chloride solution in water (10 mL) and subsequently adding ethanol (50 mL) to the dissolved product to precipitate a purified product. The precipitate was collected by filtration, washed with ethanol, and dried under vacuum at about 50° C. The purified product was identified as ferric gluconate complex co-precipitated with sodium chloride confirmed by the test for chloride ions using silver nitrate and was analyzed by GPC. The GPC analysis showed that the complex corresponding to the principle peak was present in greater than 95% purity and that the weight average molecular weight remained at about 45,000 Daltons. This peak corresponds to the sodium ferric gluconate peak obtained on analysis of the marketed sodium ferric gluconate in sucrose (FERRLECIT®), shown in FIG. 3.

Example 24

Preparation of Sodium Ferric Gluconate Complex

The procedure of Example 8 was followed, except the amount of the first base addition in Step 1 was 3.3 mL of 30% wt./Vol, aqueous sodium carbonate, and the ferric salt employed in Step 1 consisted of a combination of ferric chloride hexahydrate (2.5 g, 9.25 mmol) and ferric nitrate nonahydrate (3.75 g, 9.25 mmol).

The GPC analyses of the reaction aliquot and of the final purified and dried product indicated that the complex corresponding to the principle peak was present in greater than 95% purity and that the weight average molecular weight was about 45,000 Daltons.

Example 25

Isolation of Sodium Ferric Gluconate Complex via Concentration of the Reaction Mixture According to Step 2 of Example 25

The procedure of Example 8 was followed, except the reaction mixture of Step 2 was subjected to vacuum distillation to isolate the product complex as a concentrate. The resulting concentrated sodium ferric gluconate complex was diluted with 20% w/v sucrose solution in water for injection to generate an injectable iron composition. The GPC analyses of the product indicated that the complex corresponding to the principle peak was present in greater than 95% purity and that the weight average molecular weight was about 50,000 Daltons. This peak corresponds to the sodium ferric gluconate peak obtained on analysis of the marketed sodium ferric gluconate in sucrose (FERRLECIT®), shown in FIG. 3.

Example 26

Isolation of Sodium Ferric Gluconate Complex Via Concentration of the Reaction Mixture According to Step 2 of Example 6

Figure 2:
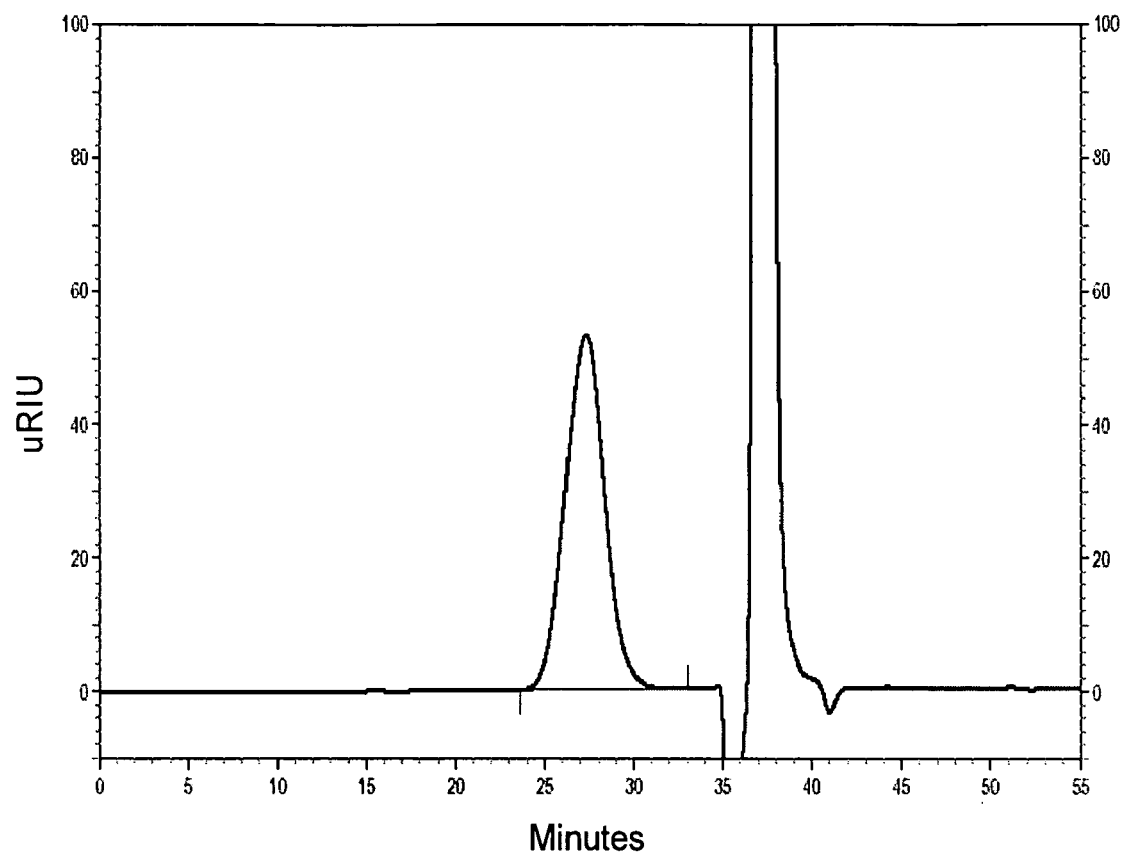
FIG. 2 shows a GPC trace of sodium ferric gluconate complex prepared by the process of the invention, having a weight average molecular weight of 50,000 Daltons.

The procedure of Example 6 was followed, except the reaction mixture of Step 2 was subjected to vacuum distillation at about 50° C. to reduce the volume of the reaction mixture to about 70% of its original volume. The resulting mixture was cooled to 25° C. and ethanol (50 mL) was added with stirring. A dark brown precipitate formed. The precipitate was collected by filtration. The collected product was purified by dissolution in a 40% (weight/volume) aqueous (water) sucrose solution (10 mL). Addition of ethanol (50 mL) to the dissolved product served to form a precipitate. This precipitate was collected by filtration, washed with ethanol and dried under vacuum at about 50° C. The product was identified as sodium ferric gluconate complex co-precipitated with sucrose. Analysis (GPC) of the purified product yielded a weight average molecular weight for the peak corresponding to the sodium ferric gluconate complex of about 50000 Daltons. The GPC analysis of the purified product is shown in FIG. 2.

Example 27

Preparation (18 mmol scale) of Sodium Ferric Gluconate Complex without Isolating Ferric Hydroxide by Filtration Step 1—Preparation of Ferric Hydroxide Ferric chloride hexahydrate (5 g) was dissolved in deionized water (20 mL) at a temperature of about 20° C. To the stirred ferric chloride solution was added sodium carbonate (3.3 mL of 30% w/v aqueous solution). The pH of the mixture was monitored using a pH meter. The temperature of the mixture was maintained at about 20° C. Following the addition of sodium carbonate, the resulting mixture was dark brown to reddish brown in color. The mixture was allowed to stand for about 30 min., during which time the pH of the reaction mixture was observed to drop to 1.7. Additional sodium carbonate solution was added as the pH of the mixture was monitored. A gelatinous precipitate appeared at a pH of about 3.0. Additional sodium carbonate solution was added until the pH of the mixture reached 4.0, yielding a suspension of ferric hydroxide.

Step 2—Preparation of the Sodium Ferric Gluconate Complex

To a 100 mL three necked round bottom flask, fitted with reflux condenser and stirrer assembly, was added water (20 mL) and sodium gluconate (12 g). The resulting mixture was heated in an oil bath maintained at 120° C. for about 10 min. The temperature of the mixture reached about 100–105° C. Sodium hydroxide (about 3 mL, 20% w/v) was added to the heated reaction mixture. Then the suspension of ferric hydroxide prepared in Step 1 was added over about 15 min. The reaction mixture formed a clear dark brown solution after the addition of the suspension of ferric hydroxide was completed. Following the addition, the temperature of the reaction mixture was maintained at about 100 to 105° C. for about 2 hrs. The reaction mixture was subsequently cooled to ambient temperature (20 to 25° C.). An aliquot of the reaction mixture was removed for GPC analysis to confirm the weight average molecular weight of the product sodium ferric gluconate complex (about 50000 Daltons).

Step 3—Isolation of the Sodium Ferric Gluconate Complex

The reaction mixture was concentrated by vacuum distillation to about 75% of the original reaction volume. Ethanol (about 50 mL) was added to the concentrated reaction mixture at 25° C. with stirring. A dark brown precipitate formed and was collected by filtration. The collected product was purified further by dissolving it in water (10 mL) and subsequently adding ethanol (50 mL) to the dissolved product to precipitate a purified product. The precipitate was collected by filtration, washed with ethanol, and dried under vacuum at about 50° C. The purified product was identified as ferric gluconate complex by confirming the content of ferric iron and the molecular weight (70,000 Daltons) by GPC. This peak corresponds to the sodium ferric gluconate peak obtained on analysis of the marketed sodium ferric gluconate in sucrose (FERRLECIT®), shown in FIG. 3.

Example 28

Preparation (180 mmol scale) of Sodium Ferric Gluconate Complex

Step 1—Preparation of Ferric Hydroxide

Ferric chloride hexahydrate (50 g) was dissolved in deionized water (200 mL) at a temperature of about 20° C. To the stirred ferric chloride solution was added sodium carbonate (33 mL of 30% w/v aqueous solution). The pH of the mixture was monitored using a pH meter. The temperature of the mixture was maintained at about 20° C. Following the addition of sodium carbonate solution, the resulting mixture was dark brown to reddish brown in color. The mixture was allowed to stand for about 30 min., during which time the pH of the reaction mixture was observed to drop to 1.7. Additional sodium carbonate solution was added as the pH of the mixture was monitored. A gelatinous precipitate appeared at a pH of about 3.0. Additional sodium carbonate solution was added until the pH of the mixture reached 4.0, yielding a suspension of ferric hydroxide. Following the addition of sodium carbonate solution, the reaction mixture was allowed to stand for about 10 minutes to allow the precipitate to settle. The precipitated ferric hydroxide was then collected by filtration and washed with water (250 mL). The wet filter cake (about 150 g) was made into a slurry in water (about 200 mL).

Step 2—Preparation of the Sodium Ferric Gluconate Complex

To a 1000 mL three necked round bottom flask, fitted with reflux condenser and stirrer assembly, was added water (200 mL) and sodium gluconate (120 g). The resulting mixture was heated in an oil bath maintained at about 120° C. for about 20 min. The temperature of the mixture reached about 100–105° C. Sodium hydroxide (about 20 mL, 20% w/v) was added to the heated reaction mixture. Then the slurry of ferric hydroxide prepared in Step 1 was added over about 15 min. The reaction mixture formed a clear, dark brown solution within one minute after the addition of the suspension of ferric hydroxide was completed. Following the addition, the temperature of the reaction mixture was maintained at about 100 to 105° C. for about 2 hrs. The reaction mixture was subsequently cooled to ambient temperature (20 to 25° C.). An aliquot of the reaction mixture was removed for GPC analysis to confirm the weight average molecular weight of the product sodium ferric gluconate complex (about 45,000 Daltons). This peak corresponds to the sodium ferric gluconate peak obtained on analysis of the marketed sodium ferric gluconate in sucrose (FERRLECIT®), shown in FIG. 3.

Step 3—Isolation of the Sodium Ferric Gluconate Complex

Ethanol (about 3000 mL) was added into the reaction mixture formed in Step 2, at 25° C. with stirring. A dark brown precipitate formed and was collected by filtration. The collected product was purified further by dissolving it in water (100 mL) and subsequently adding ethanol (500 mL) to the dissolved product to precipitate a purified product. The precipitate was collected by filtration, washed with ethanol, and dried under vacuum at about 50° C. The purified product was identified as sodium ferric gluconate complex and was analyzed by GPC.

Example 29

Preparation of Sodium Ferric Gluconate Complex and Isolation Thereof by Freeze Drying Sodium ferric gluconate complex was prepared by the process described in Steps 1 and 2 of Example 1.

After completion of Step 2, the reaction mixture was transferred to a round bottom flask and cooled to about −75° C. to freeze the reaction mixture. The frozen reaction mixture was then freeze dried using a VIRTIS, model 12 EL freeze drying apparatus at a pressure of about 25 millitorr for a time interval of about 12 hours.

Example 30

Preparation (1.8 mol scale) of Sodium Ferric Gluconate Complex and Isolation by Centrifugation Step 1—Preparation of Ferric Hydroxide Ferric chloride hexahydrate (500 g) was dissolved in deionized water (2000 mL) at a temperature of about 20° C. To the stirred ferric chloride solution was added sodium carbonate (330 mL of 30% w/v aqueous solution). The pH of the mixture was monitored using a pH meter. The temperature of the mixture was maintained at about 20° C. Following the addition of sodium carbonate solution, the resulting mixture was dark brown to reddish brown in color. The mixture was allowed to stand for about 30 min., during which time the pH of the reaction mixture was observed to drop to 1.7. Additional sodium carbonate solution was added as the pH of the mixture was monitored. A gelatinous precipitate appeared at a pH of about 3.0. Additional sodium carbonate solution was added until the pH of the mixture reached 4.0, yielding a suspension of ferric hydroxide. Following the addition of sodium carbonate solution, the reaction mixture was allowed to stand for about 10 minutes to allow the precipitate to settle. The precipitated ferric hydroxide was then collected by filtration and washed with water (2500 mL). The wet filter cake (about 1500 g) was made into a slurry in water (about 2000 mL).

Step 2—Preparation of the Sodium Ferric Gluconate Complex

To a 10 liter three-necked round bottom flask, fitted with a condenser and stirrer assembly, was added water (2000 mL) and sodium gluconate (500 g). The resulting mixture was heated in an oil bath maintained at about 120° C. for about 20 min. The temperature of the mixture reached about 100–105° C. Aqueous sodium hydroxide (about 20 mL, 20% w/v) was added to the heated reaction mixture. Then, the slurry of ferric hydroxide prepared in Step 1 was added over a time interval of about 15 min. The resulting reaction mixture formed a clear, dark brown solution within one minute after completion of the addition of the suspension of ferric hydroxide. Following the addition, the temperature of the reaction mixture was maintained at about 100 to 105° C. for about 2 hrs. The reaction mixture was concentrated to 30% of its original volume. The reaction mixture was subsequently cooled to ambient temperature (20 to 25° C.). An aliquot of the reaction mixture was removed for GPC analysis to confirm the weight average molecular weight of the product sodium ferric gluconate complex (about 45,000 Daltons).

Step 3—Isolation of the Sodium Ferric Gluconate Complex

Acetone (about 3000 mL) was added to the reaction mixture formed in Step 2, at 25° C. with stirring. A dark brown precipitate formed. The precipitate was collected by centrifugation using a Rousselet-Robatel model RC-30 centrifuge. The centrifuge was operated at about 1500 rpm. The mixture containing the precipitated sodium ferric gluconate complex was fed to the centrifuge over about 30 min, and the centrifugation was continued for about 30 minutes after the feed was complete. The collected product washed with acetone, and dried under vacuum at about 50° C. The product was identified as sodium ferric gluconate complex by GPC.

All references cited herein are incorporated by reference. The present invention may be embodied in other specific forms without departing from the spirit or essential attributes thereof and, accordingly, reference should be made to the appended claims, rather than to the foregoing specification, as indication of the scope of the invention.

What is claimed is:

1. A process of preparing sodium ferric gluconate complex, substantially free of excipients, comprising the steps of:
   (a) reacting ferric hydroxide, a sodium base and sodium gluconate, in an aqueous reaction mixture, at a pH in the range from about 7.5 to about 13; and
   (b) isolating sodium ferric gluconate complex from the aqueous reaction mixture by:
      (i) forming a mixture by adding to the aqueous reaction mixture at least one water-miscible organic solvent in an amount sufficient to precipitate sodium ferric gluconate complex from the mixture; and
      (ii) collecting the precipitated sodium ferric gluconate complex, from the mixture formed in step (i).

2. A process according to claim 1, wherein the isolated sodium ferric gluconate complex has a weight average molecular weight in the range from about 20,000 to about 150,000 Daltons.

3. A process according to claim 1, wherein the reaction mixture comprises ferric iron in an amount from about 0.2% w/w to about 8% w/w based on the weight of the reaction mixture.

4. A process according to claim 1, wherein the ferric hydroxide in step (a) is prepared by a process comprising the steps of:
   (a) providing a reaction mixture comprising a ferric salt dissolved in an aqueous medium;
   (b) adding to the reaction mixture from about 1 to about 2 equivalents of a first base based on the amount of ferric salt in the reaction mixture;
   (c) allowing the reaction mixture to equilibrate for a time interval greater than about 10 minutes;
   (d) adding a second base to the equilibrated reaction mixture; and
   (e) collecting the ferric hydroxide from the reaction mixture.

5. A process according to claim 4, wherein the first and second bases are independently selected from the group consisting of alkali metal carbonates, alkali metal bicarbonates, alkali metal hydroxides, and water-soluble amines.

6. A process according to claim 4, wherein the first and second bases are independently selected from the group consisting of sodium carbonate, sodium bicarbonate, sodium hydroxide, and tris-hydroxymethylaminoethane.

7. A process according to claim 4 wherein about one equivalent of the first base is added to the reaction mixture.

8. A process according to claim 4 wherein about two equivalents of the first base are added to the reaction mixture.

9. A process according to claim 4, wherein the first base is added to the reaction mixture until the pH of the resulting mixture is from about 2.0 to about 2.5.

10. A process according to claim 4, wherein in step (d) the second base is added in an amount sufficient to adjust the pH of the reaction mixture to a pH in the range from about 3.5 to about 9.

11. A process according to claim 10, wherein the second base is added in an amount sufficient to adjust the pH of the reaction mixture to about 4.0.

12. A process according to claim 10, wherein the second base is added in an amount sufficient to adjust the pH of the reaction mixture to about 7.0.

13. A process according to claim 10, wherein second base is added in an amount sufficient to adjust the pH of the reaction mixture to about 8.3.

14. A process according to claim 4, wherein the ferric salt is ferric chloride, ferric nitrate, or a mixture thereof.

15. A process according to claim 4, wherein the ferric hydroxide is collected by filtration.

16. A process according to claim 15, further comprising the step of forming a slurry of the collected ferric hydroxide in an aqueous solvent.

17. A process according to claim 16, wherein the aqueous solvent comprises a mixture of water and a water-miscible organic solvent.

18. A process according to claim 17, wherein the aqueous solvent comprises up to about 30% of the water-miscible organic solvent.

19. A process according to claim 1, wherein, in step (a), the molar ratio of sodium gluconate to ferric hydroxide is from about 0.2:1 to about 5:1.

20. A process according to claim 19, wherein, in step (a), the molar ratio of sodium gluconate to ferric hydroxide is from about 1:1 to about 5:1.

21. A process according to claim 1, wherein the temperature in step (a) is in the range from about 75° C. to about 120° C.

22. A process according to claim 21, wherein the temperature in step (a) is in the range from about 95° C. to about 115° C.

23. A process according to claim 1, wherein, in step (a), the sodium gluconate and ferric hydroxide are reacted for a time interval in the range from about 2 minutes to about 36 hours.

24. A process according to claim 1, wherein, in step (a), the sodium gluconate and ferric hydroxide are reacted for a time interval in the range from about 2 to about 300 minutes.

25. process according to claim 17 wherein the water-miscible organic solvent is selected from the group consisting of methanol, ethanol, acetone, tetrahydrofuran, dioxane, acetonitrile and mixtures thereof.

26. A process according to claim 1 wherein the step of collecting the precipitated sodium ferric gluconate complex comprises collecting by filtration.

27. A process according to claim 1 wherein the step of collecting the precipitated sodium ferric gluconate complex comprises collecting by centrifugation.

28. The process according to claim 1, further comprising purifying the isolated sodium ferric gluconate complex, said purifying comprising the steps of:
   (a) dissolving the isolated sodium ferric gluconate complex in an aqueous solvent;
   (b) forming a mixture by adding to the solution formed in step (a) at least one water-miscible organic solvent in an amount sufficient to precipitate purified sodium ferric gluconate complex from the solution; and
   (c) collecting the purified sodium ferric gluconate complex from the mixture formed in step (b).

29. A process according to claim 28 wherein the water-miscible organic solvent is selected from the group consisting of methanol, ethanol, acetone, tetrahydrofuran, dioxane, acetonitrile and mixtures thereof.

30. The process according to claim 28, further comprising drying the purified sodium ferric gluconate complex.

31. A process of preparing a co-precipitate comprising sodium ferric gluconate complex and sucrose, comprising the steps of:
   (a) reacting ferric hydroxide, a sodium base and sodium gluconate, in an aqueous reaction mixture, at a pH in the range from about 7.5 to about 13;
   (b) isolating sodium ferric gluconate complex from the aqueous reaction mixture by:
      (i) forming a mixture by adding to the aqueous reaction mixture at least one water-miscible organic solvent in an amount sufficient to precipitate sodium ferric gluconate complex from the mixture; and
      (ii) collecting the precipitated sodium ferric gluconate complex, from the mixture formed in step (i);
   (c) dissolving the isolated sodium ferric gluconate complex in an aqueous solvent to form a solution;
   (d) forming a mixture by adding to the solution formed in step (c) at least one water-miscible organic solvent in an amount sufficient to precipitate sodium ferric gluconate complex from the solution;
   (e) collecting the purified sodium ferric gluconate complex from the mixture formed in step (d);
   (f) dissolving purified sodium ferric gluconate complex product prepared according to step (e) in an aqueous sucrose solution;
   (g) forming a mixture by adding to the solution of sodium ferric gluconate complex formed in step (f) at least one water-miscible organic solvent in an amount sufficient to co-precipitate sodium ferric gluconate complex and sucrose; and
   (h) collecting the co-precipitate formed in step (g).

32. A process according to claim 31, further comprising the step of drying the co-precipitate.

33. A process according to claim 31, wherein the ratio of purified ferric gluconate complex to aqueous sucrose solution is in the range from about 1:0.5 to about 1:10 by weight.

34. A process according to claim 31, wherein the aqueous sucrose solution has a concentration in the range from about 10% to about 50% weight/volume.

35. A process according to claim 31, wherein the water-miscible organic solvent is selected from the group consisting of methanol, ethanol, acetone, tetrahydrofuran, dioxane, acetonitrile and mixtures thereof.

36. A process for preparing an aqueous solution of sucrose and sodium ferric gluconate complex, comprising the steps of:
   (a) reacting ferric hydroxide, a sodium base and sodium gluconate, in an aqueous reaction mixture, at a pH in the range from about 7.5 to about 13;
   (b) isolating sodium ferric gluconate complex from the aqueous reaction mixture by:
      (i) forming a mixture by adding to the aqueous reaction mixture at least one water-miscible organic solvent in an amount sufficient to precipitate sodium ferric gluconate complex from the mixture; and
      (ii) collecting the precipitated sodium ferric gluconate complex, from the mixture formed in step (i);
   (c) dissolving the isolated sodium ferric gluconate complex in an aqueous solvent to form a solution;
   (d) forming a mixture by adding to the solution formed in step (c) at least one water-miscible organic solvent in an amount sufficient to precipitate sodium ferric gluconate complex from the solution;
   (e) collecting purified sodium ferric gluconate complex from the mixture formed in step (d); and
   (f) dissolving the purified sodium ferric gluconate complex, prepared according to step (e), in a solution of sucrose in water.

37. A process of preparing an aqueous solution of sucrose and sodium ferric gluconate complex, comprising the steps of:
   (a) reacting ferric hydroxide, a sodium base and sodium gluconate, in an aqueous reaction mixture, at a pH in the range from about 7.5 to about 13;
   (b) isolating sodium ferric gluconate complex from the aqueous reaction mixture by:
      (i) forming a mixture by adding to the aqueous reaction mixture at least one water-miscible organic solvent in an amount sufficient to precipitate sodium ferric gluconate complex from the mixture; and
      (ii) collecting the precipitated sodium ferric gluconate complex, from the mixture formed in step (i);
   (c) dissolving the isolated sodium ferric gluconate complex in an aqueous solvent to form a solution;
   (d) forming a mixture by adding to the solution formed in step (c) at least one water-miscible organic solvent in an amount sufficient to precipitate sodium ferric gluconate complex from the solution;
   (e) collecting the purified sodium ferric gluconate complex from the mixture formed in step (d);
   (f) dissolving the purified sodium ferric gluconate complex formed in step (e) in an aqueous sucrose solution;
   (g) forming a mixture by adding to the sodium ferric gluconate complex solution formed in step (f) at least one water-miscible organic solvent in an amount sufficient to co-precipitate sodium ferric gluconate complex and sucrose;
   (h) collecting the co-precipitate formed in step (g); and
   (i) dissolving the collected co-precipitate in water.

38. A process of preparing an aqueous solution of sucrose and sodium ferric gluconate complex, comprising the steps of:
   combining ferric hydroxide, a sodium base and sodium gluconate, in an aqueous reaction mixture, at a temperature and at a pH in the range from about 7.5 to about 13;
   (b) maintaining the mixture at the temperature for a time interval in the range from about 5 minutes to about 36 hours; and
   (c) adding to the reaction mixture a selected quantity of sucrose.

39. The process according to claim 38, wherein the temperature in steps (a) and (b) is a temperature in the range of from about 75° C. to about 120° C.

40. The process according to claim 38, wherein the temperature in steps (a) and (b) is a temperature in the range of from about 95° C. to about 115° C.

41. The process according to claim 38, wherein, the molar ratio of sodium gluconate to ferric hydroxide is in the range from about 0.2:1 to about 5:1.

42. The process according to claim 38, wherein, the molar ratio of sodium gluconate to ferric hydroxide is in the range from about 1:1 to about 5:1.

43. A process according to claim 1 wherein the isolated sodium ferric gluconate complex comprises crystalline sodium ferric gluconate complex.

44. A process according to claim 1 wherein the isolated sodium ferric gluconate complex comprises amorphous sodium ferric gluconate complex substantially free of crystalline sodium ferric gluconate complex.

45. A process according to claim 1 wherein the isolated sodium ferric gluconate complex contains from about 1 to about 55% ferric iron by weight.

46. A process according to claim 1 wherein the isolated sodium ferric gluconate complex contains from about 1 to about 50% ferric iron by weight.

47. process according to claim 1 wherein the isolated sodium ferric gluconate complex contains from about 2 to about 15% ferric iron by weight.

48. A process according to claim 1 wherein the isolated sodium ferric gluconate complex contains from about 30 to about 50% ferric iron by weight.

49. A method according to claim 1, wherein the ferric hydroxide used in step (a) is prepared by adding at least one base to an aqueous solution of a ferric salt and separating precipitated ferric hydroxide from the solution.

50. A method according to claim 49, wherein the ferric hydroxide prepared comprises the ferric salt partially neutralized.

51. A method according to claim 1, wherein, in step (b), the sodium base is sodium hydroxide.

52. A method according to claim 31, wherein the ferric hydroxide used in step (a) is prepared by adding at least one base to an aqueous solution of a ferric salt and separating precipitated ferric hydroxide from the solution.

53. A method according to claim 52, wherein the ferric hydroxide prepared comprises the ferric salt partially neutralized.

54. A method according to claim 31, wherein, in step (a), the sodium base is sodium hydroxide.

55. A method according to claim 36, wherein the ferric hydroxide used in step (a) is prepared by adding at least one base to an aqueous solution of a ferric salt and separating precipitated ferric hydroxide from the solution.

56. A method according to claim 55, wherein the ferric hydroxide prepared comprises the ferric salt partially neutralized.

57. A method according to claim 36, wherein, in step (a), the sodium base is sodium hydroxide.

58. A method according to claim 37, wherein the ferric hydroxide used in step (a) is prepared by adding at least one base to an aqueous solution of a ferric salt and separating precipitated ferric hydroxide from the solution.

59. A method according to claim 58, wherein the ferric hydroxide prepared comprises the ferric salt partially neutralized.

60. A method according to claim 37, wherein, in step (a), the sodium base is sodium hydroxide.

61. A method according to claim 38, wherein the ferric hydroxide used in step (a) is prepared by adding at least one base to an aqueous solution of a ferric salt and separating precipitated ferric hydroxide from the solution.

62. A method according to claim 61, wherein the ferric hydroxide prepared comprises the ferric salt partially neutralized.

63. A method according to claim 61, wherein, in step (a), the sodium base is sodium hydroxide.

* * * * *

UNITED STATES PATENT AND TRADEMARK OFFICE
CERTIFICATE OF CORRECTION

| | | |
|---|---|---|
| PATENT NO. | : 7,179,939 B2 | Page 1 of 1 |
| APPLICATION NO. | : 10/889123 | |
| DATED | : February 20, 2007 | |
| INVENTOR(S) | : Jagadeesh Babu Rangisetty et al. | |

It is certified that error appears in the above-identified patent and that said Letters Patent is hereby corrected as shown below:

In column 7:

cancel the text at lines 6-9, and insert:

--Fig. 2 shows a GPC trace of sodium ferric gluconate complex coprecipitated with sucrose (in 20% aqueous solution), prepared by the process of the invention, wherein the sodium ferric gluconate complex has a weight average molecular weight of 50,000 Daltons.--;

cancel the text at lines 11-14, and insert:

--Fig. 4 shows a GPC trace of sodium ferric gluconate complex prepared by the process of the invention, having a weight average molecular weight of 25,000 Daltons.--

In column 15, line 61, "10520 C" should read --105°C--.

Signed and Sealed this

Twenty-fourth Day of March, 2009

JOHN DOLL
*Acting Director of the United States Patent and Trademark Office*